United States Patent [19]

Fabry et al.

[11] Patent Number: 4,865,774

[45] Date of Patent: Sep. 12, 1989

[54] SURFACE-ACTIVE HYDROXYSULFONATES

[75] Inventors: Bernd Fabry, Korschenbroich; Robert Piorr, Ratingen-Hoesel; Astrid Schumacher, Duesseldorf, all of Fed. Rep. of Germany

[73] Assignee: Henkel Kommanditgesellschaft auf Aktien, Duesseldorf, Fed. Rep. of Germany

[21] Appl. No.: 226,596

[22] Filed: Jul. 29, 1988

[30] Foreign Application Priority Data

Jul. 29, 1987 [DE] Fed. Rep. of Germany ....... 3725030

[51] Int. Cl.$^4$ .................. C11D 1/12; C07C 143/11
[52] U.S. Cl. ................................ 252/554; 252/535; 252/353; 252/DIG. 14; 560/264; 562/110
[58] Field of Search ............... 252/549, 554, 353, 358, 252/174.21; 560/264; 260/513 R, 513 T

[56] References Cited

U.S. PATENT DOCUMENTS

| | | | |
|---|---|---|---|
| 2,163,133 | 6/1939 | Schrauth | 260/513 R |
| 3,422,138 | 1/1969 | Holzman et al. | 260/513 T |
| 3,424,693 | 1/1969 | Stein et al. | 252/355 |
| 3,849,486 | 11/1974 | Kuehnhanss | 260/513 R |
| 4,612,142 | 9/1986 | Piorr et al. | 252/555 |

FOREIGN PATENT DOCUMENTS 3331513 3/1985 Fed. Rep. of Germany .

*Primary Examiner*—Prince E. Willis
*Assistant Examiner*—Susan Franklin
*Attorney, Agent, or Firm*—Ernest G. Szoke; Wayne C. Jaeschke; Real J. Grandmaison

[57] ABSTRACT

Aqueous solutions of surface-active hydroxysulfonates are obtained by reaction of unsaturated fatty alkenyl or fatty alkenyl polyalkoxyl esters, for example of oleyl acetate or oleyl polyethoxyl acetate, with sulfur trioxide, introduction of the reaction product into aqueous alkali metal, alkaline-earth or ammonium hydroxide and heating of the solutions until the ester and sultone groups present have been hydrolyzed.

18 Claims, No Drawings

SURFACE-ACTIVE HYDROXYSULFONATES

BACKGROUND OF THE INVENTION

1. Field of the Invention

This invention relates to a process for the production of aqueous solutions of alkali metal, alkaline-earth or ammonium salts of surface-active hydroxysulfonates from unsaturated $C_{16}$-$C_{22}$ fatty alcohols and alkoxylates thereof by sulfonation of esters of lower alkanoic acids of these alcohols and ethyoxylates, and hydrolysis of the sultone and ester groups.

On reaction with sulfur trioxide, unsaturated fatty alcohols and alkoxylation products thereof are both sulfonated at the double bond and also sulfatized at the hydroxyl group. Since sulfonate surfactants show high stability to hydrolysis while sulfate surfactants are readily hydrolyzed in acidic aqueous medium, the problem existed of producing uniform surfactants free from sulfate ester groups and stable to hydrolysis from unsaturated fatty alcohols and alkoxylates thereof.

2. Discussion of Related Art

It has already been proposed in German Patent application 33 31 513 to produce hydrolysis-stable ether sulfonates by sulfonation of the lower alkyl esters of unsaturated fatty alcohols and fatty alcohol polyalkylene glycol ethers. An even simpler process for the production of sulfonate surfactants from unsaturated fatty alcohols has now been found.

DESCRIPTION OF THE INVENTION

Other than in the operating examples, or where otherwise indicated, all numbers expressing quantities of ingredients or reaction conditions used herein are to be understood as modified in all instances by the term "about".

The present invention relates to a process for the production of aqueous solutions of alkali metal, alkaline-earth or ammonium salts of surface-active hydroxysulfonates, wherein an unsaturated fatty alkenyl or fatty alkenyl polyalkoxyl ester corresponding to formula (I)

$$R^1-O-(C_nH_{2n}O)_x-\overset{O}{\underset{\|}{C}}-R^2 \qquad (I)$$

in which $R^1$ is a linear $C_{16}$-$C_{22}$ alkenyl group or a fatty hydrocarbon group consisting essentially of oleyl, palmitoleyl, linoleyl, gadoleyl or erucyl groups, n is a number from 2 to 4, $x=0$ or is a number up to 30, and $R^2$—CO is a $C_1$-$C_4$ acyl group, is reacted with sulfur trioxide, the reaction product is introduced into an aqueous solution of 1 to 2.5 mol of alkali metal, alkaline-earth or ammonium hydroxide per mol of added $SO_3$, and the solution is heated until the ester and sultone groups present have been hydrolyzed.

Hydroxysulfonates showing particularly favorable surface-active properties are obtained where an unsaturated fatty alcohol or fatty alkyl polyalkoxyl ester corresponding to formula (I) in which $n=2$ and $x=0$ or is a number up to 10, i.e. an ester of an unsaturated fatty alcohol or of an adduct of up to 10 mol of ethylene oxide with an unsaturated fatty alcohol, is used for the sulfonation reaction. The group $R^2$—CO may be a formyl, acetyl, propionyl or butyryl group and is preferably the acetyl group. The $R^1$ group is preferably an oleyl group or a fatty hydrocarbon radical consisting essentially of oleyl groups.

The sulfonation of the unsaturated fatty alkenyl or fatty alkenyl polyalkoxyl ester corresponding to formula (I) is generally carried out with gaseous sulfur trioxide at a temperature of 10° to 80° C. The sulfonation is preferably carried out at low temperatures of 20° to 50° C. with a mixture of $SO_3$ and air or inert gas, for example nitrogen, preferably containing 1 to 10% by volume of $SO_3$. The sulfonation reaction with sulfur trioxide may be carried out continuously in a standard reactor of the type commonly used for the sulfatization of fatty alcohols or for the sulfonation of fatty acid esters, alkylbenzene or olefins, preferably of the falling film type.

The crude sulfonation product is then introduced into an aqueous solution of an alkali metal or alkaline-earth hydroxide or of ammonium hydroxide which should be present in a quantity of 1 to 2.5 mol per mol of added sulfur trioxide. The alkali hydroxide is used to neutralize the sulfonation product while the excess of alkali is necessary to neutralize the gaseous $SO_3$ dissolved in the sulfonation product and to maintain an excess of alkali which catalyzes the subsequent hydrolysis step. Sodium hydroxide is preferably used as the neutralization base.

The concentration of the neutralization base in water is preferably selected so that the end product forms a free-flowing or pumpable solution.

In addition to unsaturated ester sulfonic acids, the sulfonation product primarily contains sultones. Under the sulfonation conditions, the unsaturated fatty alkyl or fatty alkyl polyalkoxyl esters corresponding to formula i are isomerized, the position of the olefinic double bonds being statistically distributed through the alkenyl group. In the reaction of the $SO_3$ with the olefinic double bond, 1,2-sultones are probably formed first, isomerizing very quickly to 1,3-sultones and more slowly to 1,4-sultones and, at relatively high temperatures, even to unsaturated sulfonic acids.

To convert the sultones initially formed during the sulfonation reaction into hydroxysulfonates, the aqueous solution has to be subjected to a hydrolysis step. The hydrolysis is carried out by heating the solution until the sultone groups present have been completely destroyed. At the same time, the ester groups present are also hydrolyzed. The time required for the hydrolysis of the ester and sultone groups depends upon the hydrolysis conditions. At boiling temperature for example, complete hydrolysis to the hydroxysulfonate can be obtained in about 4 hours under normal pressure, taking considerably longer under pressure at higher temperatures.

Accordingly, the mixture of surface-active hydroxysulfonates obtainable by the process according to the invention consists entirely or predominantly of compounds corresponding to formula (II) or (III) as follows;

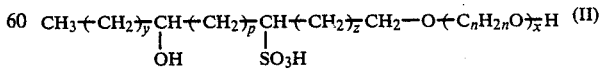

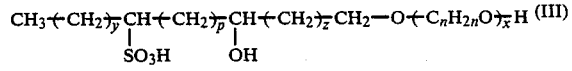

in which y and $z=0$ or a number from 1 to 18, $p=0$, 1 or 2 and the sum of $(y+z+p)$ is a number from 12 to 18, x=0 or is a number up to 30 and n is an integer from 2 to 4, or an alkali metal, alkaline-earth or ammonium salt thereof. Accordingly, the present invention also relates to these mixtures of surface-active hydroxysulfonates.

The surface-active hydroxysulfonates obtained by the process according to the invention accumulate in the form of dark yellow to light yellow, aqueous alkaline solutions of the alkali salts. If desired, these solutions may be bleached in known manner with hydrogen peroxide solution or alkali metal hypochlorite solution such as sodium hypochlorite. The pH value of the solutions may be adjusted to the neutral point using, for example, hydrochloric acid, sulfuric acid, phosphoric acid, citric acid or lactic acid. For stabilization against bacterial attack, the solutions are best preserved, for example with formaldehyde solution, p-hydroxybenzoate, sorbic acid or other known preservatives.

The fatty alkenyl or fatty alkenyl polyalkoxyl esters corresponding to formula (I) used as starting materials may be obtained by methods known from the literature. They may be produced from unsaturated fatty alcohols, for example from oleyl alcohol or technical grade alcohol cuts consisting predominantly of oleyl alcohol, palmitoleyl alcohol, linoleyl alcohol, gadoleyl alcohol or erucyl alcohol. Small amounts of saturated alcohols, for example cetyl and stearyl alcohol, are acceptable, above all when the products produced therefrom by alkoxylation are themselves soluble in water. Suitable unsaturated alcohols may be produced by hydrogenation of oleic acid or of technical grade oleic acids and are commercially available. Technical grade cetyl-oleyl and oleyllinoleyl alcohol cuts having an iodine value of from 70 to 130 are preferably used. The alkoxylation of unsaturated alcohols with ethylene oxide, propylene oxide, butylene oxide or mixtures of these alkylene oxides is a well known industrial process, giving mixtures o homologous alkoxylates of which the average degree of alkoxylation x corresponds to the molar quantity of alkenyl oxide added. The non-alkoxylated unsaturated alcohols or the adducts of up to 10 mol of ethylene oxide are preferably used.

The esterification of the terminal hydroxyl group of the unsaturated alcohols and/or their alkoxylates may also be carried out by methods known from the literature. It may be carried out, for example, by reaction with a carboxylic acid corresponding to the formula $R^2$—COOH in the presence of a catalyst, for example concentrated acid (approx. 10 ml $H_2SO_4$ per mol alcohol) or tin powder (approx. 0.05 to 0.1 mol per mol alcohol) at boiling temperature with separation of the water of reaction. However, the esterification may also be carried out by reaction with a carboxylic acid anhydride of the formula $R^2COOCOR^2$ under known conditions. The carboxylic acid or the carboxylic acid anhydride is best used in a molar excess of from about 10 to 20 mol-% for the esterification. In general, the esterification with a carboxylic anhydride is substantially complete in 2 to 4 hours, for example at a temperature corresponding to the boiling temperature of the carboxylic acid.

The hydroxysulfonates obtained by the process according to the invention show high surface activity and favorable performance properties as surfactants. The foaming behavior of the alkali metal and ammonium salts thereof is particularly favorable, in some cases clearly surpassing that of α-sulfofatty acid esters and alkyl benzenesulfonates. The alkaline-earth salts are relatively low-foaming surfactants. The products also show pronounced wetting power with respect to textile fabrics, so that they appear suitable both as technical wetting agents and for use in detergents and cleaning preparations. Their hydrolysis stability, even in acidic medium, should be particularly emphasized, considerably broadening their scope of application, for example in relation to fatty alcohol sulfates and alkyl ether sulfates.

The invention is illustrated by the following examples.

EXAMPLES

1.1 Preparation of Oleyl Acetate (Technical)

A technical grade oleyl alcohol (HD-Ocenol®90/95, iodine value 94, hydroxyl value 210) was reacted with acetic anhydride (20 mol-% excess) for 4 hours at 118° C. The reaction mixture was then poured onto ice water and the organic phase was washed repeatedly with water. The crude ester obtained was then dried and purified by distillation. The ester obtained had an iodine value of 83 and a residual hydroxyl value of 0.9.

1.2 Preparation of the Hydroxysulfonate 1.2.1 sulfonation with 1 mol $SO_3$;

310 g (1 mol) of the oleyl acetate from example 1.1 were introduced into an 800 ml standing reactor with jacket cooling and sulfonated at 30° C. with 80 g (1 mol) of $SO_3$. The $SO_3$ was driven out by heating from a corresponding quantity of oleum, diluted with $N_2$ to a concentration of 5% by volume and introduced into the oleyl acetate over a period of 32 minutes, during which time the temperature of the reaction mixture was kept by cooling at values below 40° C.

After the sulfonation, the reaction mixture was cooled to 10° C. and stirred into a dilute solution of 84 g (2.1 mol) of NaOH in 1500 g of water. This mixture was then hydrolyzed on a steam bath for 4 hours at 95° to 100° C. After cooling to 20° C., the pH value of the reaction mixture was adjusted to 7.0 by the addition of HCl solution.

The product obtained had the following characteristic data:

| | |
|---|---|
| Anionic surfactant (two-phase titration by Standard Method DGF-H-III-10): | 0.517 mval/g |
| Unsulfonated fractions (per DGF-G-III-6b): | 4.0% by weight |
| $Na_2SO_4$: | 2.0% by weight |
| $CH_3COONa$: | 6.0% by weight |
| Klett color value (1 cm cell): (after 30 minutes' bleaching with a 2% aqueous solution of sodium hypochlorite) | 82 |

1.2.2 Sulfonation with 1.3 mol $SO_3$:

The procedure used was as in example 1.2.1, 1.3 mol of $SO_3$ (104 g) being introduced into the oleyl acetate in 30 minutes. The hydroxysulfonate obtained had the following characteristic data:

| | |
|---|---|
| Anionic surfactant (per DGF-H-III-10): | 0.594 mval/g |
| Unsulfonated fractions (per DGF-G-III-6b): | 2.0% by weight |
| $Na_2SO_4$: | 2.0% by weight |
| $CH_3COONa$: | 6.0% by weight |
| Klett color value: | 280 |
| (The Klett color value was measured at a concentration of 5% by weight of anionic surfactant and at a pH value of 7 using a 1 cm cell and a blue filter (400 to 465 mμ)) | |

1.2.3 Sulfonation with 1.8 mol SO$_3$:

The procedure used was as in example 1.2.1, 1.8 mol of SO$_3$ (144 g) being introduced into the oleyl acetate in 40 minutes. The hydroxysulfonate obtained had the following characteristic data:

| | |
|---|---|
| Anionic surfactant (per DGF-H-III-10): | 0.723 mval/g |
| Unsulfonated fractions (per DGF-G-III-6b): | 2.0% by weight |
| Na$_2$SO$_4$: | 2.0% by weight |
| CH$_3$COONa: | 4.0% by weight |
| Klett color value: | 425 |

1.2.4 Sulfonation as in example 1.2.1 at 50° to 60° C.:

The procedure used was as in example 1.2.1, except the temperature of the reaction mixture was kept between 50° and 60° C. during introduction of the SO$_3$. The hydroxysulfonate obtained had the following characteristic data:

| | |
|---|---|
| Anionic surfactant (per DGF-H-III-10): | 0.516 mval/g |
| Unsulfonated fractions (per DGF-G-III-6b): | 4.0% by weight |
| Na$_2$SO$_4$: | 5.0% by weight |
| CH$_3$COONa: | 4.0% by weight |
| Klett color value: | 140 |

1.2.5 Preparation in a falling-film reactor:

In a continuous falling-film reactor, 3.1 kg (10 mol) of oleyl acetate (according to example 1.1) were reacted with SO$_3$ in a molar ratio of oleyl acetate to SO$_3$ of 1:1.3 at a temperature of 30° C. (throughput 10 g/min). The crude sulfonation product was continuously stirred into dilute aqueous sodium hydroxide and then hydrolyzed and worked up as in example 1.2.1. The product obtained had the following characteristic data:

| | |
|---|---|
| Anionic surfactant (per DGF-H-III-10): | 1.498 mval/g |
| Unsulfonated fractions (per DGF-G-III-6b): | 5.0% by weight |
| Na$_2$SO$_4$: | 1.0% by weight |
| CH$_3$COONa: | 5.0% by weight |
| Klett color value: | 48 |
| (after bleaching with 5% H$_2$O$_2$) | |

1.2.6 Neutralization with calcium hydroxide:

The procedure used was as in example 1.2.2, the reaction mixture being cooled after the sulfonation and stirred into a dilute solution of 155 g (2.1 mol) of Ca(OH)$_2$ in 1500 g of water. The mixture was then hydrolyzed on a steam bath for 8 hours at 95° to 100° C. and the insoluble calcium sulfonate precipitate was filtered off. After cooling to 20° C., the pH value of the reaction mixture was adjusted to 7.0 by addition of dilute hydrochloric acid. The product had the following characteristic data:

| | |
|---|---|
| Anionic surfactant (per DGF-H-III-10): | 0.521 mval/g |
| Unsulfonated fractions (per DGF-G-III-6b): | 4.0% by weight |
| CaSO$_4$: | 0.0% by weight |
| (CH$_3$COO)$_2$Ca: | 6.0% by weight |
| Klett color value: | 200 |

1.2.7 Neutralization with ammonia:

The procedure used was as in example 1.2.2, the reaction mixture being cooled after the sulfonation and stirred into a dilute solution of 36 g of NH$_3$ (2.1 mol) in 1500 g of water. The mixture was hydrolyzed on a steam bath for 8 hours at 95° to 100° C. After cooling to 20° C., the pH value of the reaction mixture was adjusted to 7.0 by addition of dilute hydrochloric acid. The product had the following characteristic data:

| | |
|---|---|
| Anionic surfactant (per DGF-H-III-10): | 0.419 mval/g |
| Unsulfonated fractions (per DGF-G-III-6b): | 5.0% by weight |
| (NH$_4$)$_2$SO$_4$: | 4.0% by weight |
| CH$_3$COONH$_4$: | 1.0% by weight |
| Klett color value: | 140 |

2.1 Preparation of Oleyl Ethoxyl(1 EO) Acetate

A technical grade oleyl alcohol (according to example 1.1) was ethoxylated in known manner (Na methylate as catalyst, 170° C.) with 1 mol of ethylene oxide per mol of oleyl alcohol. The ethoxylate was converted into the acetate as in example 1.1.

2.2 Preparation of the Hydroxysulfonate

A hydroxysulfonate having the following characteristic data was obtained from 230 g of the product of example 2.1 by sulfonation as in example 1.2.1 with 1.2 mol of SO$_3$ per mol of oleyl ethoxyl acetate introduced over a period of 12 minutes and working up as in example 1.2.1:

| | |
|---|---|
| Anionic surfactant (per DGF-H-III-10): | 0.487 mval/g |
| Unsulfonated fractions (per DGF-G-III-6b): | 3.0% by weight |
| Na$_2$SO$_4$: | 3.0% by weight |
| CH$_3$COONa: | 4.0% by weight |
| Klett color value | 114 |

3.1 Preparation of Oleyl Polyethoxyl(5 EO) Acetate 5 mol of ethylene oxide were added onto a technical grade oleyl alcohol (according to example 1.1) as in example 2.1. The ethoxylate was then converted into the acetate, again as in example 1.1.

3.2 Preparation of the Hydroxysulfonate

A hydroxysulfonate having the following characteristic data was obtained from 320 g of the oleyl polyethoxyl(5 EO) acetate obtained according to example 3.1 by sulfonation as in example 1.2.1 with 1.3 mol of SO$_3$ per mol of the oleyl polyethoxyl(5 EO) acetate introduced over a period of 11 minutes and working up as in example 1.2.1:

| | |
|---|---|
| Anionic surfactant (per DGF-H-III-10): | 0.362 mval/g |
| Unsulfonated fractions (per DGF-G-III-6b): | 6.0% by weight |
| Na$_2$SO$_4$: | 3.0% by weight |
| CH$_3$COONa: | 3.0% by weight |
| Klett color value: | 21 |

4.1 Preparation of Oleyl Polyethoxyl(10 EO) Acetate 10 mol of ethylene oxide were added onto a technical grade oleyl alcohol (according to example 1.1) as in example 2.1. The ethoxylate was then converted into the acetate, again as in example 1.1.

4.2 Preparation of the Hydroxysulfonate

A hydroxysulfonate having the following characteristic data was prepared from 540 g of the oleyl polyethoxyl(10 EO) acetate according to example 4.1 by sulfonation as in example 1.2.1 with 1.3 mol of SO$_3$ per mol of oleyl polyethoxyl(10 EO) acetate introduced

| Anionic surfactant (per DGF-H-III-10): | 0.242 mval/g |
|---|---|
| Unsulfonated fractions (per DGF-G-III-6b): | 6.0% by weight |
| Na$_2$SO$_4$: | 3.0% by weight |
| CH$_3$COONa: | 3.0% by weight |
| Klett color value: | 19 |

5. Performance Tests

The hydroxysulfonates of examples 1 to 4 were performance-tested for their foaming properties and wetting power.

Foaming power:

Foaming power was determined by shaking 100 ml of a solution of 1 g/of the anionic surfactant under standard conditions in a 250 ml shaking cylinder. The volume of foam above the solution was read off 0, 1, 3 and 5 minutes after shaking. The determination was carried out at 20° C. in deionized water (0° Gh).

Wetting power

Wetting power was determined in accordance with DIN 53901 "Determination of Wetting Power by the Immersion Wetting Method." Solutions of 1 g/of anionic surfactant in deionized water (0° Gh) at 20° C. were used. The wetting effect is expressed as the time taken by a small standardized cloth to be completely wetted and to sink after immersion in the wetting agent solution.

The results of the foaming and wetting tests are shown in the following Table I in the form of average values of five determinations:

TABLE I

| Product of Example | Foam Volume (ml) | | | | Wetting time (seconds) |
|---|---|---|---|---|---|
| | 0 min | 1 min | 3 mins | 5 mins | |
| 1.2.1 | 300 | 170 | 60 | 18 | 91 |
| 1.2.2 | 300 | 180 | 100 | 20 | 28 |
| 1.2.3 | 200 | 145 | 10 | 0 | 93 |
| 1.2.4 | 190 | 130 | 10 | 0 | 180 |
| 1.2.5 | 300 | 170 | 60 | 25 | 32 |
| 1.2.6 | 10 | 10 | 8 | 8 | 300 |
| 1.2.7 | 230 | 170 | 110 | 40 | 13 |
| 2.2 | 300 | 200 | 150 | 75 | 220 |
| 3.2 | 300 | 200 | 190 | 150 | 261 |
| 4.2 | 300 | 200 | 150 | 100 | 300 |

We claim:

1. A process for the production of an aqueous solution of an alkali metal alkaline-earth or ammonium salt of a surface-active hydroxysulfonate, comprising reacting with gaseous sulfur trioxide at a temperature of 10° to about 80° C. an unsaturated fatty alkenyl or fatty alkenyl polyalkoxyl ester corresponding to formula (I)

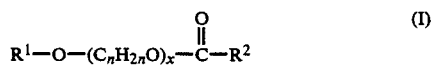

in which R$^1$ is a linear C$_{16}$-C$_{22}$ alkenyl group or a fatty hydrocarbon group consisting essentially of an oleyl, palmitoleyl, linoleyl, gadoleyl or erucyl group, n is a number from 2 to 4, x=0 or is a number up to 30, and R$^2$—CO is a C$_1$-C$_4$ acyl group; introducing the reaction product into an aqueous solution of about 1 to about 2.5 mol of alkali metal, alkaline-earth or ammonium hydroxide per mol of added SO$_3$; and heating the solution until the ester and sultone groups present have been hydrolyzed.

2. A process as in claim 1 wherein n=2, and x=0 or is a number up to 10.

3. A process as in claim 1 wherein R$^2$—CO is a formyl, acetyl, propionyl or butyryl group.

4. A process as in claim 1 wherein the reaction with sulfur trioxide is carried out at a temperature of about 20° to about 50° C. with a mixture of SO$_3$ and air or an inert gas containing about 1 to about 10% by volume of SO$_3$.

5. A process as in claim 1 wherein R$^1$ is an oleyl group or a fatty hydrocarbon radical consisting essentially of oleyl groups.

6. A process as in claim 1 including recovering a mixture of surface-active hydroxysulfonates consisting essentially of compounds corresponding to formula (II) or (III)

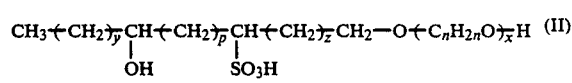

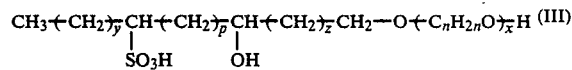

in which y and z=0 or a number from 1 to 18, p=0, 1 or 2 and the sum of (y+z+p) is a number from 12 to 18 and x=0 or is a number up to 30 and n is an integer from 2 to 4, or an alkali metal, alkaline-earth or ammonium salt thereof.

7. An aqueous solution of an alkali metal, alkaline-earth or ammonium salt of a surface-active hydroxysulfonate prepared by the process comprising reacting with gaseous sulfur trioxide at a temperature of 10° to about 80° C. an unsaturaed fatty alkenyl or fatty alkenyl polyalkoxyl ester corresponding to formula (I)

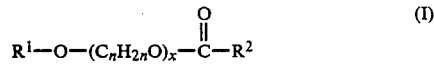

in which R$^1$ is a linear C$_{16}$-C$_{22}$ alkenyl group or a fatty hydrocarbon group consisting essentially of an oleyl, palmitoleyl, linoleyl, gadoleyl or erucyl group, n is a number from 2 to 4, x=0 or is a number up to 30, and R$^2$—CO is a C$_1$-C$_4$ acyl group; introducing the reaction product into an aqueous solution of about 1 to about 2.5 mol of alkali metal, alkaline-earth or ammonium hydroxide per mol of added SO$_3$; and heating the solution until the ester and sultone groups present have been hydrolyzed.

8. An aqueous solution as in claim 7 wherein n=2, and x=0 or is a number up to 10.

9. An aqueous solution as in claim 7 wherein R$^2$—CO is a formyl, acetyl, propionyl or butyryl group.

10. An aqueous solution as in claim 7 wherein the reaction with sulfur trioxide is carried out at a temperature of about 20° to about 50° C. with a mixture of SO$_3$ and air or an inert gas containing about 1 to about 10% by volume of SO$_3$.

11. An aqueous solution as in claim 7 wherein R$^1$ is an oleyl group or a fatty alkyl radical consisting essentially of oleyl groups.

12. An aqueous solution as in claim 7 comprising a mixture of surfaceactive hydroxysulfonates consisting essentially of compounds corresponding to formula (II) or (III)

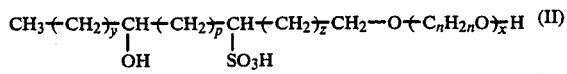 (II)

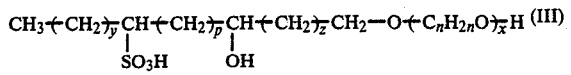 (III)

in which y and z=0 or a number from 1 to 18, p=0, 1 or 2 and the sum of (y+z+p) is a number from 12 to 18 and x=0 or is a number up to 30 and n is an integer from 2 to 4, or an alkali metal, alkaline-earth or ammonium salt thereof.

13. The process of preparing a cleaning composition comprising adding thereto an alkali metal, alkaline-earth or ammonium salt of a surface-active hydroxysulfonate prepared by the process comprising reacting with gaseous sulfur trioxide at a temperature of 10° to about 80° C. an unsaturated fatty alkenyl or fatty alkenyl polyalkoxyl ester corresponding to formula (I)

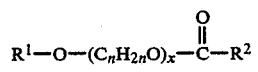 (I)

in which $R^1$ is a linear $C_{16}$–$C_{22}$ alkenyl group or a fatty hydrocarbon group consisting essentially of an oleyl, palmitoleyl, linoleyl, gadoleyl or erucyl group, n is a number from 2 to 4, x=0 or is a number up to 30, and $R^2$—CO is a $C_1$–$C_4$ acyl group; introducing the reaction product into an aqueous solution of about 1 to about 2.5 mol of alkali metal, alkaline-earth or ammonium hydroxide per mol of added $SO_3$; and heating the solution until the ester and sultone groups present have been hydrolyzed.

14. The process as in claim 13 wherein n=2, and x=0 or is a number up to 10.

15. The process as in claim 13 wherein $R^2$—CO is a formyl, acetyl, propionyl or butyryl group.

16. The process as in claim 13 wherein the reaction with sulfur trioxide is carried out at a temperature of about 20° to about 50° C. with a mixture of $SO_3$ and air or an inert gas containing about 1 to about 10% by volume of $SO_3$.

17. The process as in claim 13 wherein $R^1$ is an oleyl group or a fatty hydrocarbon radical consisting essentially of oleyl groups.

18. The process as in claim 13 wherein said hydroxysulfonate comprises a mixture of surface-active hydroxysulfonates consisting essentially of compounds corresponding to formula (II) or (III)

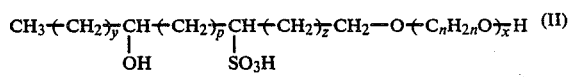 (II)

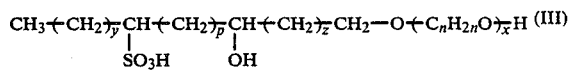 (III)

in which y and z=0 or a number from 1 to 18, p=0, 1 or 2 and the sum of (y+z+p) is a number from 12 to 18 and x=0 or is a number up to 30 and n is an integer from 2 to 4, or an alkali metal, alkaline-earth or ammonium salt thereof.

* * * * *